United States Patent [19]

Reimann

[11] Patent Number: 5,530,136
[45] Date of Patent: Jun. 25, 1996

[54] PROCESS FOR THE PREPARATION OF PILOCARPINE DERIVATIVES FROM A 5-FORMYL-IMIDAZOLE DERIVATIVE

[75] Inventor: Eberhard Reimann, Munich, Germany

[73] Assignee: Merck Patent Gesellschaft mit beschrankter Haftung, Darmstadt, Germany

[21] Appl. No.: 318,935

[22] Filed: Oct. 6, 1994

[30] Foreign Application Priority Data

Oct. 7, 1993 [DE] Germany .......................... 43 34 135.7

[51] Int. Cl.⁶ .................... C07D 405/06; C07D 233/60; C07B 37/10; C07F 9/54; C07F 9/40; C07F 7/18
[52] U.S. Cl. .................. 548/315.4; 548/110; 548/112; 548/341.1; 548/341.5
[58] Field of Search .................... 548/110, 112, 548/315.4, 341.5, 341.1

[56] References Cited

U.S. PATENT DOCUMENTS

| | | | |
|---|---|---|---|
| 4,394,151 | 7/1983 | De Fraine et al. | 548/341.5 X |
| 4,517,367 | 5/1985 | Skotsch et al. | 546/276 |
| 4,628,104 | 12/1986 | Dickens et al. | 548/341.5 |
| 5,180,837 | 1/1993 | Heywang et al. | 548/315.4 |

OTHER PUBLICATIONS

H. Link et al., Helvetica Chimica Acta—vol. 55, No. 108, pp. 1053–1063. (1972).

*Primary Examiner*—Floyd D. Higel
*Attorney, Agent, or Firm*—Millen, White, Zelano, & Branigan

[57] ABSTRACT

The invention relates to a process for the preparation of pilocarpine derivatives from a 5-formyl-imidazole derivative of the formula II

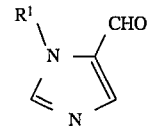

in which R¹ is hydrogen, a low molecular weight straight-chain or branched alkyl chain having 1–8 C atoms, or a substituted or unsubstituted carbocyclic radical.

10 Claims, No Drawings

PROCESS FOR THE PREPARATION OF PILOCARPINE DERIVATIVES FROM A 5-FORMYL-IMIDAZOLE DERIVATIVE

The invention relates to a process for the preparation of pilocarpine derivatives from a 5-formyl-imidazole derivative of the formula II.

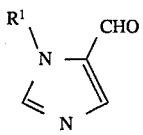

in which $R^1$ is hydrogen, a low molecular weight straight-chain or branched alkyl chain having 1–8 C atoms or a substituted or unsubstituted carbocyclic radical.

Of particular interest is the derivative where $R^1$=methyl, which is a precursor of pilocarpine and can be converted into this in a known manner.

BACKGROUND OF THE INVENTION

Pilocarpine, an imidazole alkaloid, is the subject of numerous investigations on account of its varied pharmacological properties. Its outstanding pharmacological activities include diaphoretic effects, stimulation of the parasympathetic system, miotic actions and, in particular, applications in ophthalmology.

Processes for the preparation of racemic and optically active pilocarpine are known. All these processes are characterized, however, by a comparably large number of synthesis steps, only low overall yields being achieved.

In the synthesis of H. Link and K. Bernauer (Helv. Chem. Acta 55, 1053 (1972)), racemic pilosinine is used as a precursor of pilocarpine. The starting material employed was 5-formyl-1-methylimidazole which is easily accessible from sarcosine in a few steps. The process of Link and Bernauer comprises the Stobbe condensation of an imidazole derivative with succinic acid diester to give a monomaleate whose regioselective reduction leads to butenolide formation, from which pilosinine is produced by catalytic reduction in the last step. The disadvantage of this process is the poor course of the Stobbe condensation, where yields of at most 20% are achieved.

In U.S. Pat. No. 5,180,837, a process for the preparation of racemic pilosinine derivatives from 5-formyl-1-methylimidazole is described. By conversion of the imidazole derivative to a thioacetal, deprotonation thereof and Michael addition to γ-crotonolactone and final desulfurization, the pilosinine derivative is accessible as a pilocarpine precursor. The disadvantage of the process described there is the low overall yield.

SUMMARY OF THE INVENTION

An object of the present invention is to find a process for the preparation of pilocarpine derivatives from easily accessible starting materials, which proceeds in high yields and largely without by-products.

This object was surprisingly achieved by the process according to the invention by means of a double olefination reaction and subsequent hydrogenation.

The invention therefore relates to a process for the preparation of pilocarpine derivatives of the formula I, recited below, which is characterized in that a) a 5-formylimidazole derivative of the formula II

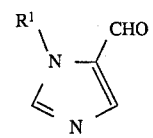

in which $R^1$ is hydrogen, alkyl having 1–8 C atoms, or a carbocyclic radical, is condensed with a suitable 2-alkoxyacetic acid ester of the formula III

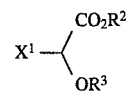

where $R^2$ and $R^3$ in each-case independently of one another are alkyl having 1–6 C atoms or $Si(R^6)s$ and $X^1$ is a radical of the formula $P(O)(OR^4)_2$, $P(R^5)_3$ or $Si(R^6)_3$, in which $R^4$, $R^5$ and $R^6$ in each case independently of one another are $C_{1-6}$-alkyl or phenyl, to give an unsaturated carboxylic acid ester of the formula IV

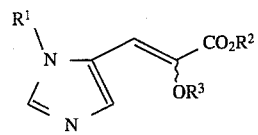

where $R^1$, $R^2$ and $R^3$ have the meaning indicated above, and the ⌇ bond indicates the cis- and trans- configuration of the component, b) the carboxylic acid ester is reduced to the alcohol of the formula V

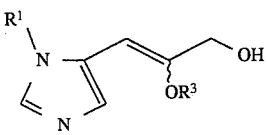

c) this is converted using an acid to the hydroxyketone of the formula VI

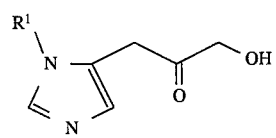

d) the hydroxyketone thus obtained is converted using a suitable carboxylic acid, activated in the 2-position, of the formula VII

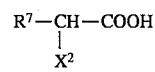

in which $X^2$ has one of the meanings of $X^1$, and $R^7$ is alkyl having 1–8 C atoms, or a carbocyclic radical, or its reactive derivatives, to an activated ester of the formula VIII

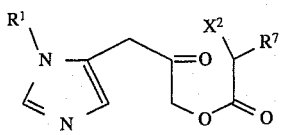

where R¹, R⁷ and X² have the meaning indicated, e) the cyclization of the ester to the lactone ring is carried out under the action of a strong base with the formation of the dehydropilocarpine derivative of the formula IX

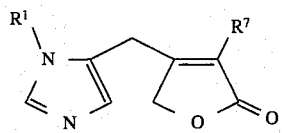

which is converted by known processes to the pilocarpine derivative of the formula I

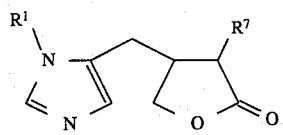

The compounds of the formulae IV, V, VI, and VIII are novel and thus likewise a subject of the invention.

If one of the radicals R¹ to R⁷ is an alkyl radical, it may be a straight-chain or branched alkyl. Examples thereof include methyl, ethyl, n-propyl, n-butyl, n-pentyl, n-hexyl, n-heptyl, n-octyl, i-propyl, 1-(or 2-)methylpropyl, tert-butyl, 1-(2- or 3-)methylbutyl, neopentyl, 1-(2- ,3- or 4-)methylpentyl, 1-(2- ,3- ,4- or 5-)methylhexyl or 2-ethylhexyl (i-octyl). It is preferably methyl, ethyl or i-propyl, in particular methyl or ethyl.

If R¹ and/or R⁷ is a carbocyclic radical, it may be an aromatic, cycloaliphatic or araliphatic carbocyclic radical, preferably of 6 to 20 carbon atoms. Preferred examples thereof include phenyl, benzyl, cyclohexyl, 1-indanyl, tetrabenzocycloheptyl (e.g., 1,2,3,4-tetrahydro-1-naphthyl), benzocycloheptyl (e.g., 5-benzocycloheptyl), 9,10-dihydro-9-anthracenyl,9H-fluoren-9-yl,5-dibenzo[a,d]cycloheptyl or dihydronaphthyl (e.g., 1,2-dihydro-1-naphthyl).

The above-mentioned carbocyclic radicals can, in each case, be unsubstituted or substituted by 1 to 6 substituents selected from the groups alkyl, alkoxy having 1–5 C atoms and halogen.

Compounds in which R¹ is methyl, ethyl or propyl, preferably methyl, are particularly preferred. Compounds of the formula VIII, where R⁷ is a straight-chain alkyl radical having 1–5 C atoms, preferably ethyl, are furthermore preferred.

From the 5-formylimidazole derivative of the formula II, which is easily accessible from sarcosine methyl ester hydrochloride and dimethylamino-2-azaprop-2-en-1-ylidenedimethylammonium, as described in EP 0 366 250, using suitable 2-alkoxyacetic acid esters of the formula III, in particular phosphorus organyls, of the formula

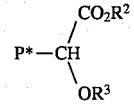

where P* is P(R⁵)₃ or P(O)(OR⁴)₂, in which R⁴ and R⁵, in each case, independently of one another are alkyl or aryl, the unsaturated esters of the formula IV in the cis- and transconfigurations can be prepared in the presence of a base. Thus, for example, phosphoranes [P*=P(R⁵)₃] can be used for the olefination of aldehydes of the formula II after conversion to the corresponding ylides under the conditions of a Wittig reaction according to the processes described in Houben-Weyl, Methoden der Organischen Chemie [Methods of organic chemistry], Vol. 5/1b, p. 383, phosphonates [P*=P(O)(OR⁴)₂] after formation of the anion under the conditions of a Horner-Emmons reaction in analogy to the processes described, e.g., in Organic Reactions, Vol. 25, John Wiley, New York, 1978, Chapter 2, or phosphine oxides in, for example, the manner described in Houben-Weyl, Methoden der Organischen Chemie, Vol. XII/1, p. 167. Preferably, phosphonates are employed, since the phosphate esters formed during the reaction are water-soluble. Suitable bases for the preparation of a reactive phosphorus ylide, phosphonate or phosphine oxide anion are, depending on the deprotonation ability of the phosphorus organyl employed, e.g., alkali metal hydroxides such as sodium hydroxide or potassium hydroxide, alkali metal carbonates such as sodium carbonate or potassium carbonate, alkoxides such as sodium methoxide, sodium ethoxide, lithium ethoxide or potassium tert-butoxide, alkali metal amides such as potassium amide or sodium amide, alkali metal organyls such as methyllithium, n-butyllithium, tert-butyllithium or phenyllithium, organic bases such as lithium diisopropylamide or sodium methylsulfinylmethylide or hydrides such as sodium hydride or potassium hydride.

The reaction is expediently carried out in an inert solvent. Suitable inert solvents are preferably ethers such as diethyl ether, ethylene glycol dimethyl ether, tetrahydrofuran or dioxane, and amides such as dimethylformamide, hexamethylphosphoramide, dimethylacetamide or N-methylpyrrolidone, and also sulfoxides such as dimethyl sulfoxide or sulfolane as well as hydrocarbons such as pentane, hexane, cyclohexane, benzene or toluene. According to the reactivity of the phosphorus organyl employed, the reaction temperatures are expediently between about –10° C and about 150° C., preferably between 20° and 100° C., the reaction times between 1 and 48 hours.

In the reduction of the ester of the formula IV to the alcohol of the formula V, metal hydrides are preferably employed, such as, e.g., lithium aluminum hydride, sodium aluminum hydride, sodium borohydride, lithium borohydride, sodium bis(2-methoxyethoxy) aluminum hydride, stannyl hydrides such as, e.g., tributyltin hydride and in particular diisobutylaluminum hydride.

Depending on the nature of the reducing agent, suitable solvents are water, alcohols such as methanol, ethanol, isopropanol, t-butanol or n-butanol, ethers such as tetrahydrofuran, dioxane or diethyl ether, and hydrocarbons such as pentane, cyclohexane, hexane, benzene, toluene or xylene or mixtures of the solvents mentioned. The reaction temperature is dependent both on the metal hydride employed and on the solvent. The reactions are preferably carried out between 0° and 100° C. and the reaction times are between 15 minutes and 6 hours.

The hydrolysis of the enol ether of the formula V is preferably carried out using a mineral acid such as, e.g., phosphoric acid, hydrochloric acid or sulfuric acid or N-chlorosuccinimide or ammonium chloride. The hydrolysis takes place at temperatures in the range from 0° to 100° C. The salt initially produced in the hydrolysis, of the formula VIa

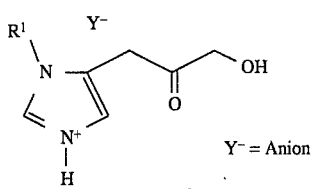

VIa

Y⁻ = Anion is converted using an alcoholic metal alkoxide solution at temperatures of 0°–100° C., preferably at room temperature, to the hydroxyketone of the formula VI. Suitable metal alkoxides are potassium or sodium methoxide or ethoxide.

The esterification of the alcohol of the formula VI with an acid of the formula VII, where $R^7$ and $X^2$ have the meaning indicated, $R^7$ preferably being methyl, ethyl, propyl, butyl or pentyl, in particular ethyl, or its reactive carboxylic acid derivatives, such as, for example, acyl halides, anhydrides, carboxylic esters and amides, is carried out by methods as are described, for example, in Houben-Weyl, Methoden der Organischen Chemie, Vol. VIII, pp. 359–680.

In a preferred process, the preparation of the ester of the formula VIII can also be carried out by the dicyclohexylcarbodiimide (DCC) method. In the reaction the addition of an acylating catalyst has proven advantageous, since this largely suppresses the tendency to form undesired N-acylureas and thereby increases the yield. Acylation catalysts used are pyridines and pyridine derivatives, preferably aminopyridines, in particular 4-dimethylaminopyridine (DMAP) or 4-(1-pyrrolidinyl)pyridine in amounts of 3–10 mol %. The reaction takes place at temperatures between 0° and 100° C., preferably in the boiling range of the solvent used.

Suitable solvents are particularly chlorinated hydrocarbons such as chloroform, dichloromethane and tetrachloromethane, and all aprotic solvents, preferably acetone, acetonitrile, dimethylformamide, dimethyl sulfoxide and ethers such as dioxane, tetrahydrofuran or diethyl ether.

The cyclization of the ester to the lactone ring is carried out by conversion of the activated ester of the formula VIII to the corresponding anion. The anion is prepared analogously as described in the preparation of the unsaturated carboxylic acid ester of the formula IV.

The addition of crown ethers, preferably 0.8 to 2.5 mol relative to the base employed, has proven advantageous in the cyclization reaction. Particularly when using sodium or potassium hydride or sodium or potassium carbonate as a base, the cyclization proceeds in high yields under mild conditions in the presence of 18-crown-6 or 15-crown-5.

The cyclization reaction is preferably carried out at room temperature or in the boiling range of the solvent used.

The pilocarpine derivative of the formula I is obtained by catalytic hydrogenation of the dehydropilocarpine of the formula IX. The catalytic hydrogenation is carried out, for example, at temperatures between about 0° C. and 200° C., and at pressures between about 1 and 200 bar in an inert solvent such as, for example, an alcohol such as methanol, ethanol, isopropanol, an ether, such as, for example, diethyl ether, tetrahydrofuran (THF) or dioxane, an ester such as, for example, ethyl acetate or methyl acetate, a carboxylic acid such as, for example, acetic acid or a hydrocarbon such as cyclohexane, cyclopentane, benzene or toluene. Suitable catalysts are particularly those which allow stereoselective hydrogenation. Suitable catalysts are preferably Raney nickel or noble metals such as platinum or palladium, which can be employed in the form of their oxides, e.g., $PtO_2$, PdO on a support, or as palladium on active carbon, calcium carbonate or strontium carbonate, or in finely divided form.

When using suitable chiral reducing agents, e.g., 1,1'-binaphthyl-2,2'-dioxyaluminum hydride or chiral hydrogenation catalysts, preferably rhodium complexes of chiral diphosphines, e.g., (6,6-dimethylbiphenyl- 2,2-diyl)bis(dicyclohexylphosphine), to convert the dehydropilocarpine, it is possible to prepare optically active pilocarpine.

The process according to the invention thus allows the preparation of pilocarpine and its derivatives from imidazole derivatives in a simple manner and in high yields in a few synthesis steps from easily accessible starting substances and is thus a significant advance in the field of pilocarpine synthesis.

The Examples below are intended to illustrate the invention without representing a limitation.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application No. P 43 34 135.7, filed Oct. 7, 1993, are hereby incorporated by reference.

EXAMPLES

The following abbreviations are used:

| THF | Tetrahydrofuran |
|---|---|
| DIBAH | Diisobutylaluminum hydride |
| DMAP | 4-Dimethylaminopyridine |
| DCC | Dicyclohexylcarbodiimide |

Example 1

Step I:

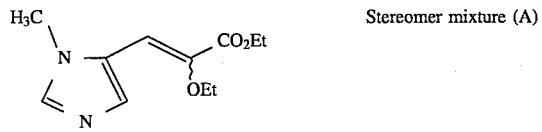

Stereomer mixture (A)

0.14 mol of ethyl diethylphosphonoethoxyacetate is slowly added dropwise with stirring and under inert gas to a suspension of 0.14 mol of NaH (paraffin-free) in 250 ml of abs. THF, the mixture is stirred for 1 h at 20° C. and a solution of 0.093 mol of 1-methylimidazole-5-aldehyde in 100 ml of abs. THF is added dropwise. After stirring at 20° C. for 10 min, the solvent is distilled off in vacuo, the residue is taken up in a little $H_2O$, and the solution is acidified with 1N HCl and washed several times with ether. The aqueous phase is rendered alkaline using 2N NaOH with cooling (0°–5° C.) and extracted several times with $CH_2Cl_2$. After drying of the organic extracts with $Na_2SO_4$, the solvent is removed in vacuo.

Yield: 99% of theory—the crude product is pure enough for the subsequent reaction.

Step II:

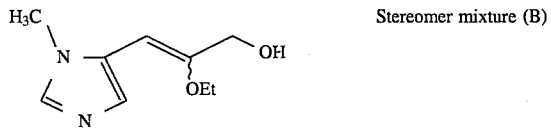

Stereomer mixture (B)

122 ml of 45% DIBAH solution (=328 mmol) are slowly added dropwise under inert gas, with stirring and ice cooling, to a solution of 137 mmol of A in 600 ml of abs. $C_6H_6$. Stirring of the mixture is continued for a further 30 min at 0°–5° C. and 600 ml of $CH_3OH$, then 100 ml of $H_2O$, are slowly added. The hydroxide precipitate is filtered off with suction and washed several times with hot CH₃OH. After drying of the combined filtrates with Na₂SO₄, the solvents are distilled off in vacuo and the residue is crystallized using C₂H₅OH.

Yield: 100% of theory. The crude product is pure enough for the subsequent reaction. Recrystallization of an analytical sample from CH₃OH/acetone: m.p. 129° C.

Step III:

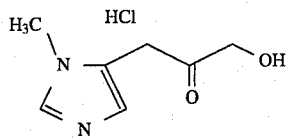   C

A solution of 58 mmol of B in 116.6 ml of N HCl (=116.6 mmol) is stirred at 30°–35° C. for 1.5 h and concentrated in vacuo at the same temperature. The residual HCl is removed by distillation with CHCl₃ in vacuo. After seeding, the residue crystallizes at 20° C. (15 h). The crystallizate is filtered off with suction, washed with a little CH₃OH and dried in vacuo.

Yield: 86% of theory; m.p. 190° C.

Step IIIa:

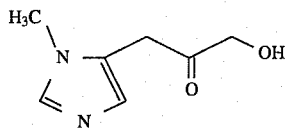   D

About 80–90% of the equivalent amount of NaOCH₃ solution in CH₃OH is slowly added dropwise at 20° C. with stirring and exclusion of moisture to a suspension of 21.24 mmol of C in 80 ml of CH₃OH, in the course of which the pH of 6.5 is not to be exceeded. The solvent is distilled off in vacuo at a maximum of 30° C. and the residue is purified by flash chromatography (silica gel; CHCl₃/CH₃OH=17:3).

Yield: 100% of theory; viscous, orange-colored oil.

Step IV:

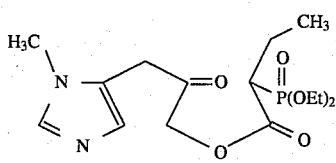   E

Catalytic amounts of DMAP and a solution of 21.3 mmol of D in 80 ml of CH₂Cl₂ are added to a solution of 26.44 mmol of 2-diethylphosphonobutyric acid in 40 ml of purified CH₂Cl₂. After cooling to 0°–5° C., a solution of 23.5 mmol of DCC in 60 ml of CH₂Cl₂ is added dropwise and the mixture is stirred for 1 h at 0°–5° C. and for 2 h at 20° C. The crystallized dicyclohexylurea is filtered off with suction and the filtrate is washed with H₂O and saturated NaHCO₃ solution. After drying of the organic phase with Na₂SO₄, the solvent is distilled off at 30° C. in vacuo and the residue is purified by flash chromatography (silica gel; ethyl acetate/CH₃OH=20:3 or CHCl₃/CH₃OH=30:3).

Yield: 95% of theory of a viscous, orange-colored oil.

Step V (Variant a):

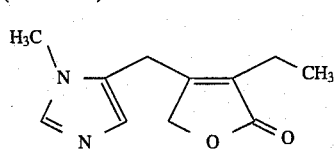   F

A mixture of 5 mmol each of 80% NaH and 15-crown-5 in 50 ml of absol. toluene is stirred at 20° C. under inert gas for 10 min and a solution of 5 mml of E in 50 ml of absol. toluene is then added dropwise. Stirring is continued for a further 15 min under inert gas and the mixture is hydrolyzed with a little water until phase separation is detectable. After separating off the organic phase, the aqueous layer is saturated with NaCl and extracted several times with CHCl₃. The combined organic phases are dried with Na₂SO₄, the solvent is distilled off at 40° C. in vacuo and the residue is purified twice by flash chromatography (silica gel; ethyl acetate/CH₃OH=20:3).

Yield: 52% of theory; virtually colorless oil.

Step V (variant b):

A solution of 0.54 mmol of E in 25 ml of absol. toluene is added rapidly at 20° C. with stirring and under inert gas to a mixture of 3.21 mmol of K₂CO₃ and 6.42 mmol of 18-crown-6 in 20 ml of toluene. Stirring of the mixture is continued for a further 15 min, a little water is added until phase separation is detectable and the organic phase is separated off. The aqueous phase is saturated with NaCl and extracted several times with CHCl₃. After drying of the combined organic phases with Na₂SO₄, the solvents are distilled off in vacuo at 40° C. and the residue is purified by flash chromatography (silica gel; ethyl acetate/CH₃OH=20:3).

Yield: 52% of theory

Step VI:

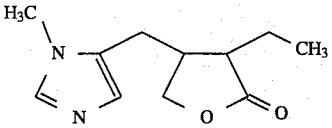   G 1.36 mmol of F in 15.5 ml of CH₃OH are hydrogenated for 5 h at 50 bar and 60° C. using 210 mg of Pd/carbon (10%). After filtering off the catalyst and distilling off the solvent at 30° C. in vacuo, the oily residue (about 250 mg) is treated with 10 ml of 1N HCl and the mixture is stirred for 3 h at 20° C. The hydrochloric acid is distilled off in vacuo at 35°–40° C., the oily residue is taken up in a little CH₃OH and ether is added. The precipitate is recrystallized from CH₃OH/ether.

Yield: 73% of theory; m.p. 210° C. NMR spectrum identical with that of the (+)-enantiomer HCl.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for the preparation of a pilocarpine compound of the formula I, comprising a) reacting a 5-formylimidazole compound of the formula II

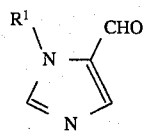   II in which $R^1$ is hydrogen, alkyl having 1–8 C atoms, or an aromatic, cycloaliphatic or araliphatic carbocyclic radical of 6–20 carbon atoms optionally substituted with 1–6 halogen atoms or alkyl or alkoxy group of 1–5 carbon atoms, with a 2-alkoxyacetic acid ester of the formula III

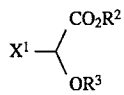

where

R² and R³ in each case independently of one another are alkyl having 1–6 C atoms or Si(R⁶)₃ and X¹ is a radical selected from the formulae P(O)(OR⁴)₂, P(R⁵)₃ or Si(R⁶)₃, in which

R⁴, R⁵ and R⁶ in each case independently of one another are C₁₋₆-alkyl or phenyl, to produce an unsaturated carboxylic acid ester of the formula IV

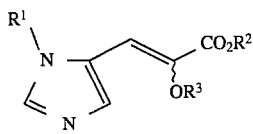

where

R¹, R² and R³ have the meaning indicated above, b) reducing the carboxylic acid ester of formula IV to produce an alcohol of the formula V

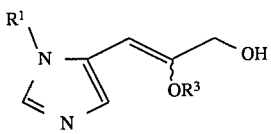

c) reacting the alcohol of formula V with of an acid to produce a hydroxyketone of the formula VI

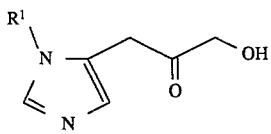

d) reacting the hydroxyketone of formula VI with a carboxylic acid activated in the 2-position of the formula VII

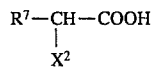

in which

X² has one of the meanings of X¹, and

R⁷ is alkyl having 1–8 C atoms, or an aromatic., cycloaliphatic or araliphatic carbocyclic radical of 6–20 carbon atoms optionally substituted with 1–6 halogen atoms or alkyl or alkoxygroups of 1–5 carbon atoms, or with an acyl halide, anhydride, carboxylic ester or amide of the carboxylic acid to produce an activated ester of the formula VIII

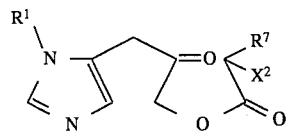

where R¹, R⁷ and X² have the meanings indicated, e) cyclizing the ester of formula VII to form a lactone ring in the presence of a strong base forming a dehydropilocarpine compound of the formula IX

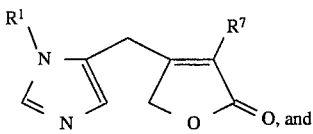

f) catalytically hydrogenating the dehydropilocarpine compound to a pilocarpine compound of the formula I

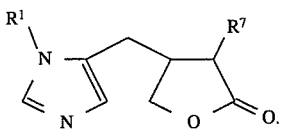

2. The process of claim 1, wherein the hydroxyketone of the formula VI is reacted with an acid of the formula VII or with an acyl halide, anhydride, carboxylic ester or amide of the carboxylic acid and dicyclohexylcarbodiimide in the presence of an acylating catalyst.

3. The process of claim 1, wherein the acylating catalyst is 4-dimethylaminopyridine or 4-(1-pyrrolidinyl)pyridine.

4. The process of claim 1, wherein the cyclization of the activated ester of the formula VIII in step (e) is conducted in the presence of a crown ether.

5. The process of claim 4, wherein 0.8–2.5 mol of the crown ether are employed, relative to the strong base used.

6. The process of claim 1, wherein in step c), the alcohol of formula V is hydrolyzed in the presence of a mineral acid to obtain a salt of the hydroxyketone of formula VI which is converted to the hydroxyketone of formula VI with an alcoholic metal alkoxide solution.

7. The process of claim 1, wherein in formulae I, II, IV, V, VI, VIII and IX, R¹ is a straight-chain or branched alkyl of 1–6 carbon atoms, a cyclohexane ring or a benzyl radical optionally substituted by alkyl or alkoxy of 1–5 carbon atoms or halogen.

8. The process of claim 1, wherein, in formula III, X¹ is of the formula P(O)(OR⁴)₂.

9. The process of claim 1, wherein reducing of the carboxylic acid ester of formula IV, step (b), is conducted in the presence of a metal hydride reducing agent.

10. The process of claim 1, wherein the catalytic reduction, step (f), is conducted in the presence of a chiral hydrogenating catalyst and the compound of formula I obtained is optically active.

* * * * *